United States Patent
Dhawan et al.

(10) Patent No.: US 12,018,130 B2
(45) Date of Patent: *Jun. 25, 2024

(54) ALKOXYLATED (HYDROXYALKYL)AMINOPHENOL POLYMERS AND METHODS OF USE

(71) Applicant: Ecolab USA Inc., St. Paul, MN (US)

(72) Inventors: Ashish Dhawan, Aurora, IL (US); Carter M. Silvernail, Burnsville, MN (US)

(73) Assignee: Ecolab USA Inc., St. Paul, MN (US)

( * ) Notice: Subject to any disclaimer, the term of this patent is extended or adjusted under 35 U.S.C. 154(b) by 249 days.

This patent is subject to a terminal disclaimer.

(21) Appl. No.: 17/507,007

(22) Filed: Oct. 21, 2021

(65) Prior Publication Data

US 2022/0119577 A1    Apr. 21, 2022

Related U.S. Application Data

(60) Provisional application No. 63/094,597, filed on Oct. 21, 2020.

(51) Int. Cl.
| | |
|---|---|
| *C08G 8/36* | (2006.01) |
| *C02F 1/40* | (2023.01) |
| *C08G 8/10* | (2006.01) |
| *C08G 8/16* | (2006.01) |
| *C08G 8/22* | (2006.01) |
| *C10G 29/22* | (2006.01) |

(52) U.S. Cl.
CPC .............. *C08G 8/36* (2013.01); *C02F 1/40* (2013.01); *C08G 8/10* (2013.01); *C08G 8/16* (2013.01); *C08G 8/22* (2013.01); *C10G 29/22* (2013.01); *C08G 2261/1422* (2013.01); *C08G 2261/1424* (2013.01); *C08G 2261/31* (2013.01); *C10G 2300/206* (2013.01)

(58) Field of Classification Search
CPC ... C08G 8/36; C08G 8/10; C08G 8/16; C08G 8/22; C08G 2261/1422; C08G 2261/1424; C08G 2261/31; C02F 1/40; C10G 29/22; C10G 2300/206

See application file for complete search history.

(56) References Cited

U.S. PATENT DOCUMENTS

| | | | |
|---|---|---|---|
| 2,518,577 A | 8/1950 | Thompson et al. | |
| 2,797,152 A | 6/1957 | Hughes et al. | |
| 2,864,797 A | 12/1958 | De Groote et al. | |
| 2,907,801 A | 10/1959 | Johnson et al. | |
| 3,010,912 A | 11/1961 | Hardman | |
| 3,678,113 A | 7/1972 | Klopfer | |
| 3,696,050 A | 10/1972 | Werts, III et al. | |
| 3,697,275 A | 10/1972 | Hayakawa et al. | |
| 3,959,358 A | 5/1976 | Jursich | |
| 4,003,800 A | 1/1977 | Bacha et al. | |
| 4,038,434 A | 7/1977 | Young | |
| 4,117,238 A | 9/1978 | Ackermann et al. | |
| 4,337,103 A | 6/1982 | Elrick et al. | |
| 4,374,742 A | 2/1983 | Evans et al. | |
| 4,585,796 A | 4/1986 | Alig et al. | |
| 4,654,451 A | 3/1987 | Miller et al. | |
| 4,675,444 A | 6/1987 | Matsunaga et al. | |
| 4,692,544 A | 9/1987 | Goerner et al. | |
| 4,744,881 A | 5/1988 | Reid | |
| 5,103,032 A | 4/1992 | Turner et al. | |
| 5,213,699 A | 5/1993 | Babiarz et al. | |
| 5,219,480 A | 6/1993 | Gutierrez et al. | |
| 5,266,442 A | 11/1993 | Ooms | |
| 5,320,765 A | 6/1994 | Fetterman, Jr. et al. | |
| 5,340,369 A | 8/1994 | Koch et al. | |
| 5,443,596 A | 8/1995 | Junino et al. | |
| 5,476,973 A | 12/1995 | Hatano et al. | |
| 5,583,247 A | 12/1996 | Nesvadba et al. | |
| 5,728,872 A | 3/1998 | Riemenschneider | |
| 5,763,144 A | 6/1998 | Jeganathan | |
| 5,909,337 A | 6/1999 | Tyndall, III | |
| 6,024,769 A | 2/2000 | Cotteret | |
| 6,040,482 A | 3/2000 | Harris et al. | |
| 6,452,020 B1 | 9/2002 | Batlaw et al. | |
| 6,639,026 B2 | 10/2003 | Eldin | |
| 7,045,647 B2 | 5/2006 | Benage | |
| 7,204,858 B2 | 4/2007 | Desenne et al. | |
| 7,498,467 B2 | 3/2009 | Shiraki | |

(Continued)

FOREIGN PATENT DOCUMENTS

| | | |
|---|---|---|
| CA | 467388 A | 8/1950 |
| DE | 343151 C | 10/1921 |

(Continued)

OTHER PUBLICATIONS

Kluchesky et al. "Polymerization Inhibition and Stopping Agents", Ind. Eng. Chem., 41: pp. 1768-1771 (1949).
Voronkov et al. "XRN=2846043" Journal of General Chemistry of the USSR, vol. 48, 2 pages, abstract (1978).
Ladona et al. "Biotransformation and Clearance of 3-(Phenylamino)propane-1,2-diol, a Compound Present in Samples Related to Toxic Oil Syndrome, in C57BL/6 and A/J Mice", Chem. Res. Toxicol., 12: pp. 1127-1137 (1999).
Zeinalova et al. "Inhibition of the oxidation of synthetic oils at high temperatures", Chemistry and Technology of Fuels and Oils, 13: pp. 40-42 (1977).
Habib et al. "Synthesis of Some Novel Antioxidantand Anticorrosive Additives for Egyptian Lubricating Oils" Petroleum Science and Technology, 30: pp. 2435-2449 (2012).

(Continued)

*Primary Examiner* — Shane Fang
(74) *Attorney, Agent, or Firm* — Kagan Binder, PLLC

(57) ABSTRACT

Disclosed herein are polymers formed by the condensation of bis(hydroxycarbyl)-aminophenolic compounds with aldehydes. The condensation polymers include one or more repeat units having bis(hydroxycarbyl)amino functionality. The hydroxyl groups of the bis(hydroxycarbyl)amino functionalities are available for further condensation with an epoxide, such as ethylene oxide, to yield a polyalkoxylated polymer. The polymers are useful as antipolymerants, polymerization retardants, surfactants, or a combination of these in one or more industrial systems.

16 Claims, No Drawings

(56) References Cited

U.S. PATENT DOCUMENTS

| | | |
|---|---|---|
| 7,569,615 B2 | 8/2009 | Leinweber et al. |
| 7,671,098 B2 | 3/2010 | Leinweber et al. |
| 7,900,590 B2 | 3/2011 | Cleveland et al. |
| 7,902,317 B2 | 3/2011 | Kumar et al. |
| 8,530,397 B2 | 9/2013 | Bera et al. |
| 9,168,217 B2 | 10/2015 | Schweinsberg |
| 9,212,330 B2 | 12/2015 | Bolton et al. |
| 9,266,797 B2 | 2/2016 | Colorado, Jr. et al. |
| 10,308,886 B2 | 6/2019 | Rana et al. |
| 2001/0050700 A1 | 12/2001 | Smith et al. |
| 2002/0156136 A1 | 10/2002 | Hortrup et al. |
| 2003/0065177 A1 | 4/2003 | Sheridan et al. |
| 2003/0111331 A1 | 6/2003 | Chalfant et al. |
| 2003/0217418 A1 | 11/2003 | Fadel et al. |
| 2005/0209117 A1 | 9/2005 | Friedrich et al. |
| 2008/0045666 A1 | 2/2008 | Snell et al. |
| 2008/0090742 A1 | 4/2008 | Mathur |
| 2012/0056128 A1 | 3/2012 | Thoret Bauchet |
| 2013/0186629 A1 | 7/2013 | Leonard et al. |
| 2019/0117541 A1 | 4/2019 | Consoli et al. |
| 2020/0172831 A1 | 6/2020 | Dhawan et al. |
| 2020/0339503 A1 | 10/2020 | Dhawan et al. |
| 2020/0339880 A1 | 10/2020 | Masere et al. |

FOREIGN PATENT DOCUMENTS

| | | |
|---|---|---|
| EP | 0145588 A2 | 6/1985 |
| EP | 0449546 A1 | 10/1991 |
| GB | 748856 A | 5/1956 |
| GB | 2030581 A | 4/1980 |
| GB | 1567047 A | 5/1980 |
| JP | 6340570 A | 12/1994 |
| RU | 2046804 C1 | 10/1995 |
| WO | 2005037206 A2 | 4/2005 |
| WO | 2020113218 A2 | 6/2020 |

OTHER PUBLICATIONS

Ionova et al. "Synthesis, Structure, and Properties of New Antioxidants Based on Hydroxypropylated p-Aminodiphenylamine", Petroleum Chemistry, 51(6): pp. 454-457 (2011).

International Search Report issued in International Application No. PCT/US2021/056024, dated Feb. 16, 2022, 5 pages.

Written Opinion issued in International Application No. PCT/US2021/056024, dated Feb. 16, 2022, 9 pages.

International Search Report issued in International Application No. PCT/US2021/056028, dated Feb. 16, 2022, 5 pages.

Written Opinion issued in International Application No. PCT/US2021/056028, dated Feb. 16, 2022, 8 pages.

ALKOXYLATED (HYDROXYALKYL)AMINOPHENOL POLYMERS AND METHODS OF USE

FIELD OF THE INVENTION

The present invention generally relates to polymeric compositions based on the condensation of phenolic compounds with aldehydes, and alkoxylated adducts thereof.

BACKGROUND

Polymeric compounds are used throughout industry to assist people in achieving important manufacturing and processing goals. Benefits in industrial processes such as inhibiting corrosion, inhibiting biofilm formation, inhibiting microbial growth, modifying rheology, emulsifying, demulsifying, tackifying, plasticizing, defoaming, flocculating, coagulating, and the like are achieved by practitioners using a variety of polymeric compounds. Thus, polymeric surfactants, emulsifiers, bio-film inhibitors, biocides, rheology modifiers, anti-corrodents, emulsion breakers, fuel dehazers, asphaltene dispersants, defoaming additives, flocculants/coagulants, and the like are generally available in the industry to append one or more industrial processes or assist in reaching one or more industrial manufacturing, processing, transporting, or storage goals.

An industrially important class of polymers is phenol-aldehyde type polymers, including prepolymers and cured resins (collectively "phenolic polymers" or "phenolics"). Phenolics are synthesized by condensing phenolic monomers such as phenol, resorcinol, Bisphenol A, alkylphenols, and/or mixtures of these with aldehydes such as formaldehyde. An industrially useful form of phenolic is a phenolic prepolymer. Phenolic prepolymers are commercially available as water-based dispersions including the partial reaction product of one or more phenolic monomers and formaldehyde. In such form, the prepolymer is relatively stable in the water dispersion. Since formaldehyde exists predominantly in solution as a dynamic equilibrium of methylene glycol oligomers, the concentration of the reactive form of any "free" formaldehyde residing in the prepolymer formulation depends on temperature and pH. Commercially available phenolic prepolymers include novalacs and resoles.

Novalacs are phenolic prepolymer dispersions wherein the molar ratio of formaldehyde to phenolic monomer is less than one, and wherein curing is accomplished using acid or base catalysis, in some embodiments employing heat, along with the addition of an aldehyde or a formaldehyde donor such as hexamethylene tetramine. Examples of suitable novalac cure catalysts include oxalic acid, hydrochloride acid, and sulfonic acid. The prepolymer units are mainly linked by methylene and/or ether groups through the methylolation of the phenolic monomer by the reactive form of formaldehyde. Resoles are phenolic prepolymer dispersions having a formaldehyde to phenolic monomer ratio of greater than one (for example, around 1.5). The resoles are cured after drying using heat and a base catalyst.

To form a phenolic prepolymer dispersion, phenolic monomer, aldehyde, water and catalyst are mixed in the desired amount and heated, for example to between about 50° C. and 100° C. or between about 60° C. and 80° C. to form the prepolymerized dispersion. The prepolymers will crosslink, in embodiments upon heating to around 120° C., to form methylene and dibenzyl ether bridges via elimination of both the water of dispersion and the water formed by the polycondensation reaction. The result is a stable, three-dimensional cured network. The final crosslinking step results in a phenolic resin possessing industrially recognized characteristics such as excellent hardness, thermal stability, and chemical imperviousness.

Alkylphenol-based phenolics, or "alkylphenolics" are structurally similar to phenolics formed from phenol and/or resorcinol and are synthesized using any of the foregoing processes wherein an alkylphenol is employed in place of, or in combination with, phenol, resorcinol, and the like. The alkylphenol monomer employed to synthesize the alkylphenolic is typically a 4-alkylphenol, e.g. 4-nonylphenol wherein the nonyl moiety is linear or branched. Alkylphenolic prepolymers and resins have improved solubility in hydrocarbon solvents compared to their non-alkylated counterparts. Industrially, alkylphenolics are employed to build green tack and impart adhesion strength in rubber-based adhesives, and are useful as modifiers for rubber materials such as butyl rubber, chloroprene rubber, and the like, imparting improved oil resistance, heat resistance, chemical resistance, and weathering properties to rubber products such as belts, treads, hoses, vehicle tires, and the like.

The alkylphenol monomer employed in the majority of industrial alkylphenolics is nonylphenol, which is often more accurately described as a highly branched C9 4-alkylphenol. Nonylphenol-formaldehyde condensation polymers provide a favorable solubility profile and cost effectiveness combination for industrial use. Cost effectiveness of the nonylphenol monomer is due to historically widespread industrial adoption of ethoxylated phenol surfactants, which are highly effective nonionic surfactants. However, nonylphenol and other alkylphenols, as the breakdown products of their ethoxylated adducts in the environment, have been restricted in many countries. Nonylphenols are now recognized to be endocrine disruptors and xenoestrogens in humans and aquatic animals. Accordingly, nonylphenol ethoxylates are being replaced by other surfactants, for example alkanol ethoxylates, in many international markets. Similarly, there is a need in the industry to replace alkylphenolics due to the desirability of eliminating use of alkylphenols generally and nonylphenols particularly.

Development of environmentally benign monomers that are usefully employed to form polymers possessing new and useful properties are an ongoing need in the industry. Further, there is a need in the industry to provide alternatives for alkylphenolics, including both prepolymers and resins.

SUMMARY OF THE INVENTION

Described herein are polyalkoxylated polymers and compositions comprising them. The polyalkoxylated polymers are polyalkoxylated (hydroxyalkyl)aminophenol polymers comprising a polyalkoxylated repeat unit having the structure

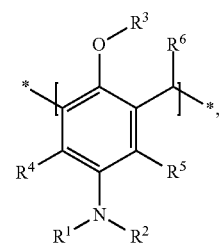

wherein $R^1$ and $R^2$ are $-(CR^7R^8)_n(CHOR^9)(CH_2)_p(O)_qR^{10}$;

$R^3$ is $[R^{11}O]_xH$;

$R^4$ and $R^5$ are independently H, $C_1$-$C_{22}$ alkyl, or $-[R^{11}O]_xH$;

$R^6$ is H, alkyl, aryl, benzyl, or aralkyl, optionally substituted with an alkyl group, alkoxy group, or hydroxyl group;

$R^7$ and $R^8$ are independently H or alkyl;

$R^9$ is H or $-[R^{11}O]_xH$;

$R^{10}$ is $C_1$-$C_{24}$ linear, branched, or cyclic alkyl, aryl, or aralkyl;

each $R^{11}$ is independently $-CH_2-CH_2-$, $-CH(CH_3)-CH_2-$, $-CH_2-CH_2-CH_2-$, $-CH_2-CH_2-CH_2-CH_2-$, or $-CH(C_6H_6)-CH_2-$;

n is an integer between 1 and 12;

p is 0 or an integer between 1 and 12;

q is 0 or 1; and each x is independently an integer between 2 and 1000.

In embodiments, $R^4$ and $R^5$ are H. In embodiments, $R^7$ and $R^8$ are H. In embodiments, n, p, and q are 1. In embodiments, $R^{10}$ is selected from n-octyl, isooctyl, n-decyl, isodecyl, n-dodecyl, n-tetradecyl, n-hexadecyl, n-hexyl, n-butyl, isobutyl, t-butyl, n-pentyl, isopentyl, or 2-ethylhexyl. In embodiments, $R^6$ is H.

In embodiments, at least one $R^{11}$ is $-CH_2-CH_2-$. In embodiments, at least one $R^{11}$ is $-CH(CH_3)-CH_2-$. In embodiments, each $R^6$ is $-CH_2-CH_2-$. In embodiments, each $R^{11}$ is $-CH(CH_3)-CH_2-$. In embodiments, $-[R^{11}O]_xH$ is characterized as an alkylene oxide functionality. In some embodiments, $-[R^{11}O]_xH$ is characterized as a copolymeric alkylene oxide functionality. In some embodiments of the copolymeric alkylene oxide functionality, each $R^{11}$ is either $-CH_2-CH_2-$ or $-CH(CH_3)-CH_2-$. In some embodiments, the copolymeric alkylene oxide functionality is a block copolymeric alkylene oxide functionality. In embodiments, each x is between 2 and 100.

In embodiments, the polyalkoxylated polymer comprises 1-1000 total polyalkoxylated repeat units having one or more of the foregoing structures, or is a crosslinked polyalkoxylated polymer network having at least one and in embodiments more than 1000 total polyalkoxylated repeat units.

In embodiments, methods of resolving emulsions in industrial process streams include adding one or more polyalkoxylated polymers to an industrial process stream including, consisting essentially of, or consisting of an emulsion, to form a treated process stream. Industrial process streams suitably treated by addition of the one or more polyalkoxylated HCAP resins include emulsions of crude oil and wash water formed during crude oil purification, and manufacturing process streams formed during synthesis, purification, and/or transportation of ethylenically unsaturated or "vinylic" compounds such as butadiene, styrene, acrylic acid, and the like. In embodiments, 0.1 ppm to 10,000 ppm of the one or more polyalkoxylated polymers is added to the industrial process stream or is present in the treated industrial process stream.

Other objects and features will be in part apparent and in part pointed out hereinafter.

DETAILED DESCRIPTION

Although the present disclosure provides references to preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, "substantially" means "consisting essentially of", as that term is construed in U.S. patent law, and includes "consisting of" as that term is construed in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Discussion

Disclosed herein are polyalkoxylated bis(hydroxycarbyl) aminophenolic polymers, which are polymeric compounds including one or more repeat units comprising the condensation product of a bis(hydroxycarbyl)aminophenolic (HCAP) resin with an aldehyde, further wherein each HCAP repeat unit is polyalkoxylated to include one or more polyalkylene oxide functionalities.

The polyalkoxylated HCAP resins include at least one polyalkoxylated

HCAP repeat unit according to the formula:

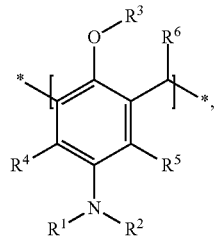

wherein $R^1$ and $R^2$ are $-(CR^7R^8)_n(CHOR^9)(CH_2)_p(O)_qR^{10}$;
$R^3$ is $[R^{11}O]_xH$;
$R^4$ and $R^5$ are independently H, $C_1$-$C_{22}$ alkyl, $-[R^{11}]_xH$, or $NR_1R_2$;
$R^6$ is H, alkyl, aryl, benzyl, or aralkyl, optionally substituted with an alkyl group, alkoxy group, or hydroxyl group;
$R^7$ and $R^8$ are independently H or alkyl;
$R^9$ is H or $-[R^{11}O]_xH$;
$R^{10}$ is $C_1$-$C_{24}$ linear, branched, or cyclic alkyl, aryl, or aralkyl;
each $R^{11}$ is independently $-CH_2-CH_2-$, $-CH(CH_3)-CH_2-$, $-CH_2-CH_2-CH_2-$, $CH_2-CH_2-CH_2-CH_2-$, or $-CH(C_6H_6)-CH_2-$;
n is an integer between 1 and 12;
p is 0 or an integer between 1 and 12;
q is 0 or 1; and
each x is independently an integer between 2 and 1000.

In embodiments, $R^4$ and $R^5$ are H. In embodiments, $R^7$ and $R^8$ are H. In embodiments, n, p, and q are 1. In embodiments, $R^{10}$ is selected from n-octyl, isooctyl, n-decyl, isodecyl, n-dodecyl, n-tetradecyl, n-hexadecyl, n-hexyl, n-butyl, isobutyl, t-butyl, n-pentyl, isopentyl, or 2-ethylhexyl.

In embodiments, $R^6$ is H. In embodiments $R^6$ is $CH_3$. In embodiments $R^6$ is COOH. In embodiments $R^6$ is benzyl. In embodiments $R^6$ is

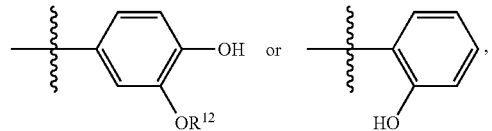

wherein $R^{12}$ is methyl or ethyl. In embodiments $R^6$ includes one or two oxygen atoms. In embodiments $R^6$ includes an ether moiety. In embodiments $R^6$ includes a hydroxyl moiety. In embodiments $R^6$ includes one or more hydroxyl moieties, one or more ether moieties, or a combination thereof. In embodiments, $R^6$ includes a crosslink moiety, for example where a bisaldehyde such as glyoxal is employed as the aldehyde in the condensation. Bisaldehydes include two aldehyde functionalities capable of condensation with HCAP functionalities and so are capable of obtaining crosslinking of the resulting HCAP polymer.

In embodiments, at least one $R^{11}$ is $-CH_2-CH_2-$. In embodiments, at least one $R^{11}$ is $-CH(CH_3)-CH_2-$. In embodiments, each $R^{11}$ is $-CH_2-CH_2-$. In embodiments, each $R^{11}$ is $-CH(CH_3)-CH_2-$. In embodiments, $-[R^{11}O]_xH$ is suitably characterized as an polyalkoxylated functionality, an alkylene oxide functionality, a polymeric alkylene oxide functionality, or a polyalkylene oxide functionality. In some embodiments, $-[R^{11}O]_xH$ is characterized as a copolymeric alkylene oxide functionality. In some embodiments of the copolymeric alkylene oxide functionality, each $R^{11}$ is either $-CH_2-CH_2-$ or $-CH(CH_3)-CH_2-$. In embodiments, a copolymeric alkylene oxide functionality is disposed in an alternating, random, or block configuration. In some embodiments, a copolymeric alkylene oxide functionality is a block copolymeric alkylene oxide functionality. In embodiments, each x is between 2 and 200.

In some embodiments, the polyalkoxylated HCAP resin comprises, consists essentially of, or consists of an alternative repeat unit that is a polyalkoxylated HCAP repeat unit having the tertiary amino functionality situated in a 1,3-relationship (that is, meta-) to the phenolic oxygen. The alternative repeat unit has the following structure:

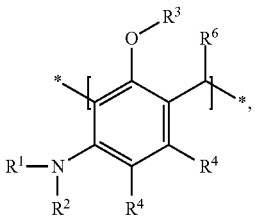

wherein $R^1$, $R^2$, $R_3$, $R^4$, $R^5$, and $R^6$ are the same as set forth above. In embodiments, the polyalkoxylated HCAP resin comprises one or more polyalkoxylated HCAP repeat units, and one or more alternative repeat units. In some embodiments, the polyalkoxylated HCAP polymer includes one or more alternative repeat units and excludes polyalkoxylated HCAP repeat units. In other embodiments, the polyalkoxylated HCAP polymer includes one or more polyalkoxylated HCAP repeat units and excludes alternative repeat units. In other embodiments, the polyalkoxylated HCAP resin includes one or more polyalkoxylated HCAP repeat units and one or more alternative repeat units. In still other embodiments, the polyalkoxylated HCAP polymer comprises, consists essentially of, or consists of one or more polyalkoxylated HCAP repeat units and one or more alternative repeat units and may be characterized as a polyalkoxylated HCAP copolymer. Thus, in embodiments, a polyalkoxylated HCAP copolymer comprises, consists essentially of, or consists of one or more polyalkoxylated HCAP repeat units, one or more alternative repeat units, or a combination thereof. In embodiments, a polyalkoxylated HCAP copolymer comprises one or more polyalkoxylated HCAP repeat units, one or more alternative repeat units, or a combination thereof and one or more additional repeat units comprising the condensation product of a phenolic compound and an aldehyde. In embodiments, the phenolic compound is phenol, resorcinol, pyrocatechol, hydroquinone, phloroglucinol, hydroxyhydroquinone, or a mixture of two or more thereof. In embodiments, the aldehyde is formaldehyde, acetaldehyde, benzaldehyde, vanillin, salicylaldehyde, glyoxal, glyoxylic acid, or a mixture of two or more thereof.

In embodiments, a polyalkoxylated HCAP resin is a an HCAP resin comprising an alkylene oxide functionality bonded to each HCAP repeat unit. In embodiments, the polyalkoxylated HCAP resin includes two alkylene oxide functionalities bonded to each HCAP repeat unit. In embodiments, a polyalkoxylated HCAP resin includes three alkylene oxide functionalities bonded to each HCAP repeat unit. In embodiments, a polyalkoxylated HCAP resin includes four or more alkylene oxide functionalities bonded to each HCAP repeat unit. Each alkylene oxide functionality includes at least 2 alkoxy repeat units, and up to 1000 alkoxy repeat units, for example 2-800, 2-600, 2-400, 2-200, 2-100, 2-80, 2-60, 2-40, 2-20, or 2-10 alkoxy repeat units.

Methods of making the polyalkoxylated HCAP resins include forming an HCAP prepolymer from an HCAP compound; converting the HCAP prepolymer to an HCAP resin; and functionalizing the HCAP resin with one or more alkylene oxide functionality. In embodiments an HCAP compound is characterized as including an aromatic ring compound having a bis(hydroxycarbyl)amino adduct bonded to the ring, at least one hydroxyl or alkoxyl group (phenolic hydroxyl group) bonded to the ring, and at least two hydrogen atoms susceptible to acid or base catalyzed condensation with an aldehyde bonded to the ring. Thus, in embodiments, the HCAP compound is a bis(hydroxycarbyl) amino adduct of, for example, phenol, resorcinol, pyrocatechol, hydroquinone, phloroglucinol, hydroxyhydroquinone, or two or more thereof. HCAP compounds are identified in copending U.S. application Ser. No. 16/860,954 as antipolymerants or polymerization retardants when added to industrial process streams for producing e.g. styrene, isoprene, butadiene, or another ethylenically unsaturated monomer. As such, the HCAP compounds are suitably employed to reduce free radical or oxidative type polymerization that occurs in such industrial process systems.

The HCAP compounds are susceptible to condensation polymerization with an aldehyde. Accordingly, in embodiments, one or more HCAP compounds are condensed with an aldehyde such as formaldehyde (including paraformaldehyde and formalin), acetaldehyde, vanillin, ethylvanillin, glyoxal, glyoxylic acid, salicylaldehyde or benzaldehyde to provide a bis(hydroxycarbyl)aminophenolic polymer (HCAP polymer) comprising one or more HCAP repeat units.

All embodiments regarding the HCAP repeat units disclosed herein are intended to be freely combinable without limitation as starting materials to form the polyalkoxylated HCAP resins disclosed herein.

In embodiments, HCAP polymers are polymers including at least one HCAP repeat unit. In some embodiments, an HCAP repeat unit is a repeat unit corresponding to a condensation product of an aldehyde with a bis(hydroxycarbyl)amino adduct of, for example, phenol, resorcinol, pyrocatechol, hydroquinone, phloroglucinol, hydroxyhydroquinone, or two or more thereof. In embodiments, HCAP polymers are formed by condensing one or more HCAP compounds with one or more aldehydes to form a polymer having at least 3 HCAP repeat units and up to 100 HCAP repeat units, for example a weight average or a number average of 3, 4, 5, 6, 7, 8, 9, 10, 15, 20, 25, 30, 35, 40, 45, 50, 55, 60, 65, 70, 75, 80, 85, 90, 95, or 100 HCAP repeat units or 3-10, 10-20, 20-30, 30-40, 40-50, 50-60, 60-70, 70-80, 80-90, or 90-100 HCAP repeat units or 3-90, 3-80, 3-70, 3-60, 3-50, 3-40, 3-30, 3-20, 3-15, 3-10, 3-9, 3-8, 3-7, 3-6, or 3-5 HCAP repeat units or 5-100, 10-100, 20-100, 30-100, 40-100, 50-100, 60-100, 70-100, 80-100, or 90-100 HCAP repeat units. In embodiments the HCAP polymer is formed by condensing an HCAP compound and formaldehyde and another aldehyde such as acetaldehyde or benzaldehyde, to form a HCAP polymer having at least 3 repeat units and up to 100 HCAP repeat units.

In embodiments, an HCAP polymer is an HCAP copolymer. HCAP copolymers include at least one HCAP repeat unit that is a first repeat unit, and a second repeat unit comprising a condensation product of a phenolic compound and an aldehyde selected from the aldehydes listed above, e.g. formaldehyde or an equivalent thereof (formalin or paraformaldehyde). Phenolic compounds are characterized as aromatic compounds having one or more hydroxyl groups bonded directly thereto. Phenolic compounds include, but are not limited to phenol, resorcinol, pyrocatechol, hydroquinone, phloroglucinol, and hydroxyhydroquinone. The HCAP copolymers include at least 3 total repeat units and up to 1000 repeat units, wherein at least one of the repeat units is an HCAP repeat unit. In some such embodiments the HCAP copolymers include 1-500 HCAP repeat units or 1-100 HCAP repeat units.

Combinations of the foregoing condensation strategies are advantageously employed to provide a wide compositional and structural range of HCAP polymer products. In embodiments the HCAP repeat unit includes two hydroxyalkyl moieties and one or more aromatic hydroxyl moieties per repeat unit. In embodiments an HCAP copolymer includes at least one HCAP repeat unit. In embodiments an HCAP homopolymer includes at least 3 HCAP repeat units.

Exemplary but non-limiting HCAP polymers include homopolymers and copolymers comprising one or more repeat units (a)-(e):

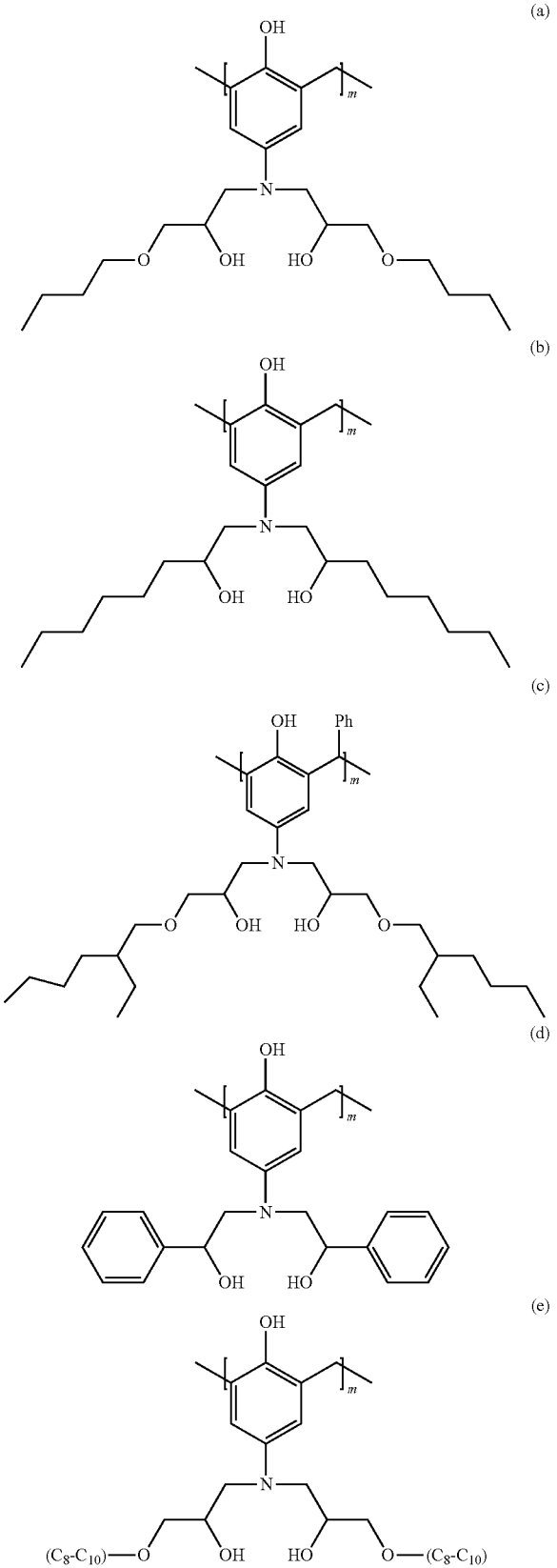

The repeat unit (a) is formed from the reaction of 4-aminophenol with butyl glycidyl ether, followed by condensation with formaldehyde. The repeat unit (b) is formed by the reaction of 4-aminophenol with 1,2-epoxyoctane, followed by condensation with formaldehyde. The repeat unit (c) is formed by the reaction of 4-aminophenol with 2-ethylhexylglycidyl ether, followed by condensation with benzaldehyde. The repeat unit (d) is formed by the reaction of 4-aminophenol with styrene oxide, followed by condensation with formaldehyde. And the repeat unit (e) is formed by the reaction of 4-aminophenol with a mixed $C_8$-$C_{10}$ alkyl glycidyl ether, followed by condensation with benzaldehyde; in some embodiments the mixed $C_8$-$C_{10}$ alkyl glycidyl ether includes a mixture of linear $C_8$-$C_{10}$ alkyl moieties, while in other embodiments the mixed $C_8$-$C_{10}$ alkyl glycidyl ether includes a mixture of linear and branched $C_8$-$C_{10}$ alkyl moieties.

The HCAP polymer as defined herein is an HCAP prepolymer, or an HCAP resin. In embodiments, an HCAP prepolymer is formed by employing the foregoing steps of condensing aldehyde and phenolic content at mild temperature, such as below 100° C. to form an HCAP prepolymer. Then the HCAP prepolymer is heated to remove the water of condensation and achieve cure (chain extension and/or crosslinking) to form an HCAP resin. In some embodiments, the ratio of aldehyde to total phenolic content is selected by the user to form a novalac type HCAP prepolymer, wherein the molar ratio of aldehyde to total phenolic content is less than 1. In some embodiments, the ratio of aldehyde to total phenolic content is selected by the user to form a resole type HCAP prepolymer, wherein the molar ratio of aldehyde to total phenolic content is greater than 1. In embodiments, the ratio of total phenolic content to aldehyde is selected by the user to be about 1:1. In some embodiments, the molar ratio of aldehyde to total phenolic content is between about 0.0005:1 to 0.8:1, or about 0.001 to 0.6:1, or about 0.1:1 to 0.4:1, or about 0.2:1 to 0.3:1. In other embodiments, the molar ratio of total phenolic content to aldehyde is between about 0.0005:1 to 0.8:1, or about 0.001 to 0.6:1, or about 0.1:1 to 0.4:1, or about 0.2:1 to 0.3:1.

In some embodiments the condensation reaction commonly employed in forming phenolic aldehyde prepolymers (novalacs and resoles) or cured phenolic resins are advantageously employed herein to form HCAP prepolymers and resins. Specifically, one or more HCAP compounds or a combination of one or more HCAP compounds and one or more additional aromatic hydroxylated compounds are selected and combined with one or more aldehydes. Additional aromatic hydroxylated compounds include phenol, alkylated phenol, resorcinol, pyrocatechol, hydroquinone, phloroglucinol, hydroxyhydroquinone, lignosulfonic acid, phenoldisulfonic acid, and oligomerized sources such as tannic acid, humic acid, fulvic acid, lignin extracts, and Quebracho extracts; and other aromatic hydroxylated compounds without limitation. One or more HCAP compounds and optionally one or more additional aromatic compounds are combined to provide a "total phenolic content" or moles of reactive functionality available for condensation with an aldehyde.

Thus, in embodiments, a selected amount of total phenolic content is combined with a selected amount of one or more aldehydes, wherein the selections provide the desired level of polymerization; and a selected, acidic or basic cure catalyst is added under conditions of mild heat, for example between between 50° C. and 120° C., or between about 60° C. and 100° C. to obtain a polymeric condensation product or prepolymer. In embodiments, the synthesis of the HCAP prepolymers is carried out in the absence of added water. In embodiments, the synthesis of the HCAP prepolymers is carried out substantially in the absence of added water, wherein "substantially" means that sufficient water is added to the reaction vessel to achieve or enable a reaction such as depolymerization of paraformaldehyde or formalin to formaldehyde. In embodiments, synthesis of the HCAP prepolymers is achieved by addition of an acid or base catalyst to the reaction vessel along with an amount of water sufficient to dissolve and/or deliver the acid or base to the reaction vessel.

In embodiments, after the condensation is completed, an HCAP prepolymer is dispersed in the selected solvent. The HCAP prepolymer is dispersed at a total solids content of 30 wt % to 90 wt % based on the weight of the dispersion, or 35 wt % to 80 wt %, or about 40 wt % to 70 wt %, or about 50 wt % to 60 wt % solids based on the weight of the dispersion.

The HCAP prepolymers are converted to HCAP resins by heating the prepolymer dispersion to at least 100° C., such as 100° C. to 180° C., or 120° C. to 150° C. The higher temperature in this stage causes methylene and dibenzyl ether bridges to form via elimination of the water formed by the condensation reaction. The HCAP prepolymers chain-extend, crosslink, or both (collectively, "cure"), in some embodiments concomitant with evaporation of the solvent, such as by coating and evaporative heating to result in the HCAP resin. In other embodiments, the HCAP prepolymer is cured by heating in the solvent, wherein the water of condensation is removed from the reaction vessel by azeotrope or by use of molecular sieves or another drying agent.

After curing, the HCAP prepolymer is converted to an HCAP resin. The HCAP resin is a three-dimensional cured network including one or more HCAP repeat units. The HCAP repeat units include at least two alkanolic hydroxyl groups, incorporated into the backbone of the HCAP polymer as (hydroxycarbyl)amino moieties. In embodiments the HCAP repeat units, or another repeat unit of an HCAP polymer, or a combination thereof further include one or more aromatic (phenolic) hydroxyl moieties. HCAP hydroxyl moieties incorporated within the HCAP polymer backbone are available for functionalization thereof to impart one or more additional properties to the HCAP resin or to change one or more properties of the HCAP resin. Thus, in embodiments, one or more HCAP resins are suitably functionalized by reaction of the alkanolic and/or aromatic hydroxyl groups to bond one or more adducts bonded thereto, to form a functionalized HCAP resin.

In embodiments, one or more HCAP resins are suitably functionalized to result in a polyalkoxylated polymer. In such embodiments, one or more HCAP resins are suitably functionalized by reaction of the alkanolic and/or aromatic hydroxyl groups to form one or more alkoxy groups bonded thereto, to form a polyalkoxylated HCAP polymer, or polyalkoxylated HCAP resin. A polyalkoxylated HCAP resin is an HCAP resin having a polyalkylene oxide moiety or functionality bonded thereto. In embodiments, the polyalkoxylated HCAP resin has one polyalkylene oxide moiety or functionality bonded to each HCAP repeat unit. In embodiments, a polyalkoxylated HCAP resin has more than one polyalkylene oxide moiety or functionality bonded to a repeat unit. In embodiments, a polyalkoxylated HCAP resin has more than one polyalkylene oxide moiety or functionality bonded to one HCAP repeat unit. In embodiments, a polyalkoxylated HCAP resin has more than one polyalkylene oxide moiety or functionality bonded to each HCAP repeat unit.

Thus, in embodiments, polyalkoxylated HCAP resins are formed by reaction of one or more HCAP resin hydroxyl groups with one or more alkylene oxides. A polyalkylene oxide moiety is a polyether moiety covalently bonded to the HCAP resin through one or more oxygen atoms of the HCAP resin hydroxyl groups, including alkanolic hydroxyl groups, aromatic hydroxyl groups, or both alkanolic and aromatic hydroxyl groups.

Alkylene oxides suitably employed to form the polyalkoxylated HCAP resins are not particularly limited. In embodiments, the alkylene oxide is ethylene oxide, propylene oxide, butylene oxide, styrene oxide, or a combination of two or more thereof. In embodiments, the alkylene oxide is a mixture of ethylene oxide and propylene oxide. In embodiments, the alkylene oxide is ethylene oxide.

In embodiments, methods of forming the polyalkoxylated HCAP resin include contacting an alkylene oxide with an HCAP resin, including any of the HCAP resins described above, under basic conditions to facilitate the ring-opening polymerization of the alkylene oxide (polyalkoxylation). In embodiments, the alkylene oxide is a liquid when contacted with an HCAP resin. In embodiments, the alkylene oxide is a gas when contacted with an HCAP resin. In some embodiments the gas is applied to the HCAP resin under a pressure in excess of atmospheric pressure, for example about 7 kPa to 700 kPa, such as 20 kPa to 600 kPa in excess of atmospheric pressure. Such pressure is achieved by enclosing an HCAP resin in a chamber designed and adapted to apply a gas under a pressure, such as a pressure vessel available from the Paar Instrument Company of Moline, IL, or a similar pressurizable chamber reactor designed and adapted to apply a pressurized gas to the chamber; and adding an alkylene oxide gas to the reactor under a pressure sufficient to initiate and propagate ring-opening polymerization of the alkylene oxide. In some embodiments it is not necessary to add heat to initiate and propagate the ring-opening polymerization. In other embodiments it is desirable to heat the polymer inside the reactor, e.g. to a temperature of 40° C.-200° C., for example 50° C. to 180° C.

In embodiments, an alkylene oxide is contacted with an HCAP resin in a selected molar ratio to form a polyalkoxylated HCAP resin having the desired number and composition of polyalkylene oxide repeat units. In embodiments, polyalkoxylation occurs on both alkanolic and phenolic (aromatic) hydroxy groups of the HCAP polymer. Polyalkylene oxide chain length is statistically built up by chain extension initiated by each of the hydroxyl groups of the HCAP polymer backbone. Thus, the number of polyalkylene oxide repeat units is easily targeted by contacting the HCAP resin with the calculated number of moles of alkylene oxide per mole of hydroxyl groups. For example, to obtain 10 ethylene oxide repeat units per hydroxyl group, an HCAP resin including 1 mole of HCAP repeat units per kg of HCAP resin, wherein each HCAP repeat unit includes two hydroxyl groups, requires contact of 20 moles of an alkylene oxide per kg of the HCAP resin to produce a polyalkoxylated HCAP resin having two polyalkylene oxide moieties bonded to each HCAP repeat unit, further wherein each polyalkylene oxide moiety includes 10 polyalkylene oxide repeat units, or about 10 polyalkylene oxide repeat units, or an average such as a number average of 10 polyalkylene oxide repeat units or a weight average of 10 polyalkylene oxide repeat units.

In embodiments, a polyalkoxylated HCAP resin includes at least 2 and as many as 1000 polyalkylene oxide repeat units per polyalkylene oxide moiety, often 2 to 800, 2 to 600, 2 to 400, 2 to 200, 2 to 100, 2 to 50, to 2 to 30 polyalkylene oxide repeat units per polyalkylene oxide moiety, or 2-25, 2-20, 2-18, 2-16, 2-14, 2-12, 2-10, 2-8, 2-6, 4-20, 4-18, 4-16, 4-14, 4-12, 4-10, 4-8, 2-14, 2-4, 4-6, 6-8, 8-10, 10-12, 12-24, 14-16, 16-18, 18-20, 20-25, or 25-30 polyalkylene oxide repeat units per polyalkylene oxide moiety; or a number average or weight average of 2, 3, 4, 5, 6, 7, 8, 9, 10, 11, 12, 13, 14, 15, 16, 17, 18, 19, 20, 22, 24, 26, 28, 30, 40, 50, 60, 70, 80, 90, 100, or more polyalkylene oxide repeat units per polyalkylene oxide moiety. In embodiments, there are two polyalkylene oxide functionalities per functionalized HCAP repeat unit. In embodiments, there are three polyalkylene oxide functionalities per functionalized HCAP repeat unit. In embodiments, there are more than three polyalkylene oxide functionalities per functionalized HCAP repeat unit, such as four, five, or even six polyalkylene oxide functionalities per functionalized HCAP repeat unit.

In embodiments, each polyalkylene oxide functionality present on a polyalkoxylated polymer disclosed here comprises or consists of polyethylene oxide repeat units, polypropylene oxide repeat units, polybutylene oxide repeat units, polystyrene oxide repeat units, or copolymeric repeat units including repeat units derived from two or more different alkylene oxides. Copolymeric alkylene oxide functionalities include random, alternating, and block copolymeric functionalities. For example, in embodiments the polyalkylene oxide functionality is a polyethylene oxide functionality. In embodiments the polyalkylene oxide functionality comprises a polyethylene oxide functionality. In some such embodiments, the polyalkylene oxide functionality is a polyethylene oxide-polypropylene oxide copolymeric functionality. In some such embodiments the polyethylene oxide-polypropylene oxide copolymeric functionality is a block copolymeric functionality including 1, 2, or 3 polyethylene oxide blocks and 1, 2, or 3 polypropylene oxide blocks.

We have found that the polyalkoxylated HCAP resins described herein are particularly useful as emulsion breakers for petroleum materials (such as asphaltenes or pygas products) entrained in water, or for inversion of water-in-oil polymer lattices in preparation for e.g. waterflooding (tertiary oil recovery) or other subterranean injection applications.

Accordingly, described herein are compositions including polyalkoxylated HCAP resins and methods of using polyalkoxylated HCAP resins for resolving emulsions of oil and water. In embodiments, the polyalkoxylated HCAP resins are used for resolving or otherwise "breaking" emulsions that form in some instances during crude petroleum extraction and/or refinement. As used herein, "emulsions" include water-in-oil emulsions, oil-in-water emulsions, and complex emulsions, wherein the emulsions include both petroleum-based and vegetable-based oil phases. In embodiments, an emulsion includes one or more of crude oil, refined oil, bitumen, condensate, slop oil, distillates, fuels, and mixtures thereof.

Additionally, the polyalkoxylated HCAP resins are useful for resolving emulsions in other industrial process streams, such as manufacturing process streams such as process streams formed during synthesis, purification, and/or transportation of ethylenically unsaturated or "vinylic" compounds such as butadiene, styrene, acrylic acid, and the like. The polyalkoxylated HCAP resins are also useful for resolving emulsions formed during synthesis, purification, and/or transportation of industrial process streams derived from vegetable sources, for example biodiesel process streams and the like.

Accordingly, methods of resolving an emulsion present within an industrial process stream comprise, consist essentially of, or consists of applying one or more polyalkoxylated HCAP resins to one or more industrial process streams comprising an emulsion, to form a treated industrial process stream. In embodiments, the treated process stream comprises a resolved emulsion. A resolved emulsion is a composition having two discrete and generally visible phases: an oil phase (or oily phase), and an aqueous phase. The phases are manifest as immiscible liquid layers, often with a visible interface between the phases. In embodiments, phase separation of a treated process stream to form a resolved emulsion occurs generally after allowing the treated industrial process stream to stand undisturbed or substantially undisturbed for a selected period of time. The period of time is selected by the operator to be between 10 minutes and 12 hours. The amount of polyalkoxylated HCAP resin applied to the industrial process stream is effective to resolve an emulsion therein. That is, a treated industrial process stream is an industrial process stream comprising, consisting essentially of, or consisting of an emulsion, and having a sufficient amount of one or more polyalkoxylated HCAP resins dissolved or dispersed therein to form a resolved process stream, or a resolved emulsion within the process stream, after allowing the treated industrial process stream to stand undisturbed or substantially undisturbed for a selected period of time. In embodiments, the aqueous phase of the resolved process stream includes one or more compounds desirably removed from the oil phase as a result of the treatment of the industrial process stream and resolution of the emulsion therein.

In embodiments, the amount of polyalkoxylated HCAP resin applied to the industrial process stream to form a treated process stream is between 0.01 ppm and 10,000 ppm, such as 0.1 ppm to 8000 ppm, 0.1 ppm to 6000 ppm, 0.1 ppm to 4000 ppm, 0.1 ppm to 2000 ppm, 0.1 ppm to 1000 ppm, 0.1 ppm to 500 ppm, 0.1 ppm to 400 ppm, 0.1 ppm to 300 ppm, 0.1 ppm to 200 ppm, 0.1 ppm to 100 ppm, 0.1 ppm to 50 ppm, 0.1 ppm to 25 ppm, 0.1 ppm to 10 ppm, 1 ppm to 8000 ppm, 1 ppm to 6000 ppm, 1 ppm to 4000 ppm, 1 ppm to 2000 ppm, 1 ppm to 1000 ppm, 1 ppm to 500 ppm, 1 ppm to 400 ppm, 1 ppm to 300 ppm, 1 ppm to 200 ppm, 1 ppm to 100 ppm, 1 ppm to 50 ppm, 1 ppm to 25 ppm, 1 ppm to 10 ppm, 5 ppm to 10 ppm, 10 ppm to 20 ppm, 20 ppm to 30 ppm, 30 ppm to 40 ppm, 40 ppm to 50 ppm, 50 ppm to 60 ppm, 60 ppm to 70 ppm, 70 ppm to 80 ppm, 80 ppm to 90 ppm, 90 ppm to 100 ppm, 50 ppm to 100 ppm, 100 ppm to 200 ppm, 200 ppm to 300 ppm, 200 ppm to 300 ppm, 300 ppm to 400 ppm, 400 ppm to 500 ppm, 500 ppm to 600 ppm, 700 ppm to 800 ppm, 800 ppm to 900 ppm, 900 ppm to 1000 ppm, 1000 ppm to 1500 ppm, 1500 ppm to 2000 ppm, 2000 ppm to 2500 ppm, 2500 ppm to 3000 ppm, 3000 ppm to 4000 ppm, 4000 ppm to 5000 ppm, 5000 ppm to 6000 ppm, 6000 ppm to 7000 ppm, 7000 ppm to 8000 ppm, 8000 ppm to 9000 ppm, or 9000 ppm to 10,000 ppm based on the weight or volume of the industrial process stream to form a treated industrial process stream.

In embodiments, to increase efficiency or ease in applying one or more polyalkoxylated HCAP resins to an industrial process stream, the one or more polyalkoxylated HCAP resins are included in a demulsifier composition that is useful for delivering a dispersion or solution of the polyalkoxylated HCAP resin to the industrial process stream to achieve resolution of an emulsion therein. Accordingly, described herein are demulsifier compositions comprising one or more polyalkoxylated HCAP resins and a solvent suitable for dissolving or dispersing the one or more polyalkoxylated HCAP resins. In embodiments, the solvent is selected from toluene, heavy aromatic naphtha, xylenes, a glycol, water, an alcohol, kerosene, propylene carbonate, paraffinic solvents, and any combination thereof. In embodiments, the alcohol is selected from methanol, ethanol, isopropanol, 2-ethyl hexanol, benzyl alcohol, and any combination thereof. In embodiments, the glycol is ethylene glycol or a glycol ether, such as ethylene glycol monobutyl ether, or a combination of ethylene glycol and glycol ethers.

In embodiments, the demulsifier compositions further include one or more additives. Suitable additives in the demulsifier compositions include corrosion inhibitors, viscosity reducers, friction reducers, scale inhibitors, clay swelling inhibitors, biocides, flow back aids, surfactants, and/or other chemical treatment additives used in crude oil production, refining and chemical processing. In embodiments, the demulsifier compositions include additional demulsifiers, such as alcohols, fatty acids, fatty amines, glycols, and alkylphenol formaldehyde condensation products. In embodiments, the demulsifier compositions exclude an alkylphenol compound, such as nonylphenol or an adduct thereof.

In embodiments, the demulsifier compositions include at least 1 wt % and up to 99.9 wt % polyalkoxylated HCAP resin, for example 1 wt % to 5 wt %, 1 wt % to 10 wt %, 5 wt % to 10 wt % 10 wt % to 15 wt %, 15 wt % to 20 wt %, 20 wt % to 25 wt %, 25 wt % to 30 wt %, 30 wt % to 35 wt %, 35 wt % to 40 wt %, 40 wt % to 45 wt %, 45 wt % to 50 wt %, 50 wt % to 55 wt %, 55 wt % to 60 wt %, 60 wt % to 65 wt %, 65 wt % to 70 wt %, 70 wt % to 80 wt %, 80 wt % to 85 wt %, 85 wt % to 90 wt %, 90 wt % to 95 wt %, 95 wt % to 99.9 wt %, 1 wt % to 20 wt %, 20 wt % to 40 wt %, 40 wt % to 60 wt %, 60 wt % to 80 wt %, 80 wt % to 99.9 wt %, 10 wt % to 30 wt %, 30 wt % to 60 wt %, 60 wt % to 90 wt %, 90 wt % to 99.9 wt %, 1 wt % to 50 wt %, or 50 wt % to 99.9 wt % polyalkoxylated HCAP resin.

Accordingly, in any one or more methods described herein, a polyalkoxylated HCAP resin is added or applied to an industrial process stream "neat", that is, as 100% solids, to obtain a treated industrial process stream. Additionally, in any one or more methods described herein, a polyalkoxylated HCAP resin is added or applied to an industrial process stream as a demulsifier composition. In some such embodiments, an operator may suitably apply or add a volume or a weight of a demulsifier composition to industrial process stream in an amount corresponding to the selected weight of polyalkoxylated HCAP resin for effective treatment of the industrial process stream.

In embodiments, a treated industrial process stream includes at least one polyalkoxylated HCAP resin in an amount that is effective to provide a treated industrial process stream. In embodiments, the effective amount of polyalkoxylated HCAP resin present in the treated industrial process stream or added to the industrial process stream to form a treated industrial process stream depends on the specific industrial process stream, the type of emulsion present in the industrial process stream that requires resolution, and the amount (by weight or volume) of the emulsion in the industrial process stream compared to the weight or volume of the industrial process stream overall. In embodiments, an effective amount of the polyalkoxylated HCAP resin added to an industrial process stream ranges from 0.1 ppm to 10,000 ppm based on the weight or volume of the industrial process stream, as set forth above.

Methods of resolving emulsions in one or more industrial process streams include adding one or more polyalkoxylated HCAP resins to an industrial process stream comprising, consisting essentially of, or consisting of an emulsion, in an amount effective to resolve the emulsion. In embodiments a treated industrial process stream comprises water, such as wash water from a refinery desalting process; an oil source, such as a crude oil; and a polyalkoxylated HCAP resin. In some such embodiments, the method further includes an initial step of mixing a water source and an oil source to form an emulsion thereof, prior to adding the one or more polyalkoxylated HCAP resins to form a treated emulsion, and finally resolving the treated emulsion. In embodiments the oil source is a crude oil. In embodiments the water source is connate, fresh water, distilled water, or water having less than 0.1 wt % total dissolved solids therein. "Resolving the treated emulsion" means forming a two-phase industrial process stream from an emulsion, such as a treated emulsion, by allowing the emulsion, such as a treated emulsion, to stand undisturbed or substantially undisturbed for a selected period of time. In embodiments, the period of time allowed to elapse is the amount of time that passes until two phases are visually confirmed. While the process of resolving a treated emulsion is not particularly limited with respect to time, generally the step of allowing the treated emulsion to stand undisturbed or substantially undisturbed is about 10 minutes to 12 hours, for example 30 minutes to 12 hours, 1 hour to 12 hours, 2 hours to 12 hours, 10 minutes to 2 hours, 1 hour to 2 hours, 1 hour to 4 hours, 1 hour to 6 hours, 1 hour to 8 hours, or 1 hour to 10 hours.

In embodiments, resolving an emulsion such as the foregoing water/oil emulsions results in a purified oil phase, since intimate contact of the oil phase and the aqueous phase within the emulsion causes a portion, or in some embodiments substantially all of the water soluble compounds desirably removed from the oil phase, to migrate into the aqueous phase within the emulsion. Subsequently, resolution of the emulsion into an oil phase and an aqueous phase obtains a purified oil phase, and an aqueous phase that includes materials such as salts and other water soluble or hydrophilic compounds and materials obtained from the emulsified oil source, in accordance with well-established chemical separation principles.

Accordingly, in embodiments, one or more polyalkoxylated HCAP resins or a demulsifier composition is suitably added to an industrial process stream comprising, consisting essentially of, or consisting of an emulsion of an oil source and a water source, during the forming of the emulsion or after forming the emulsion. Alternatively, the polyalkoxylated HCAP resin or demulsifier composition is added to the water source, or to the oil source, or to both the water source and the oil source prior to an initial step of mixing the water source and the oil source to form the emulsion. In embodiments, one or more polyalkoxylated HCAP resins are added to an industrial process stream comprising, consisting essentially of, or consisting of an emulsion of water and crude oil. In embodiments, the emulsion of water and crude oil includes between 5 wt % and 50 wt % water, wherein the balance of the emulsion is oil; for example, in embodiments the emulsion of water and crude oil includes 5 wt % to 45 wt %, 5 wt % to 40 wt %, 5 wt % to 35 wt %, 5 wt % to 30 wt %, 5 wt % to 25 wt %, 5 wt % to 20 wt %, 5 wt % to 15 wt %, or 5 wt % to 10 wt % water.

In embodiments the one or more polyalkoxylated HCAP resins are added to an industrial process stream by injecting a liquid demulsifier composition, such as a polyalkoxylated HCAP dispersion or solution, into the industrial process stream. In embodiments the industrial process stream comprises a crude oil. The liquid demulsifier composition comprises at least one polyalkoxylated HCAP resin and a solvent, and in some embodiments includes one or more additives such as the demulsifier composition additives described above.

In embodiments, the one or more polyalkoxylated HCAP resins are added continuously to an industrial process stream. In embodiments, the one or more polyalkoxylated HCAP resins are added semi-continuously to an industrial process stream. In embodiments, the one or more polyalkoxylated HCAP resins are added batchwise to an industrial process stream. The one or more polyalkoxylated HCAP resins of the present disclosure may be used in methods for demulsifying water-in-oil emulsions, oil-in-water emulsions, and complex emulsions in various production and refinery processes. Specific examples include, but are not limited to, oilfield production emulsions, refinery desalting emulsions, refined fuel emulsions, and recovered oil emulsions (e.g., crude oil slop, used lubricant oils, and recovered oils in the steel and aluminum industries). Thus, for example, in an industrial refinery desalting process, crude oil is mixed with wash water and the mixture is agitated in order to form an industrial process stream that is an emulsion. In the emulsion, salts and other contaminants may be dissolved or dispersed in the wash water. The water phase is then separated from emulsion by admixing the emulsion with an effective amount of the one or more polyalkoxylated HCAP resins.

A typical desalting process includes the use of pumps to move the incoming crude oil from storage tanks via piping through one or more heat exchangers. Wash water may be injected into the heated oil stream and the stream may be mixed by an in-line mixing device. The emulsified process stream may flow into an electrostatic desalter vessel where resolution and separation of the crude oil and water effluent occur. Injection of the one or more polyalkoxylated HCAP resins into the fluid stream can be carried out at various places along the path of the desalting process. Potential injection locations include, but are not limited to, prior to the crude oil storage tanks, on the outlet side of the crude oil storage tanks, upstream of the in-line mixer, into the wash water stream, and other potential locations.

In some embodiments, the industrial process stream is an emulsion comprising a crude oil and a water source. In embodiments, the water source in embodiments is connate, fresh water, or water having less than 0.1 wt % total dissolved solids therein as added to the crude oil.

In such industrial process streams, the effective amount of the polyalkoxylated HCAP resin added to an industrial process stream is based on the on volume of the oil. For example, the effect amount may be from about 1 ppm to about 3,000 ppm, from about 1 ppm to about 1,000 ppm, from about 1 ppm to about 500 ppm, from about 1 ppm to about 250 ppm, from about 1 ppm to about 200 ppm, from about 1 ppm to about 150 ppm, from about 1 ppm to about 100 ppm, from about 1 ppm to about 50 ppm, or from about 1 ppm to about 25 ppm, based on volume of the oil.

In embodiments, a demulsifier composition is combined with a reverse emulsion breaker and the combined composition is added to an industrial process stream comprising, consisting essentially of, or consisting of an emulsion. In embodiments the emulsion is an emulsion of crude oil and wash water. In embodiments the combined composition is added to the emulsion, the wash water, and/or the oil. In other embodiments, the reverse emulsion breaker is added separately from the demulsifier composition to the emulsion, the wash water, and/or the oil.

In some embodiments, the demulsifier composition is introduced into a crude oil emulsion by injecting the demulsifier composition beneath the surface into a subterranean cavity or well. In embodiments, injecting the demulsifier composition comprises injecting the demulsifier composition into the crude oil at the well-head. In embodiments injecting the demulsifier composition is injecting the demulsifier composition into the crude oil process stream at a selected point between the well-head and the final oil storage tank. In embodiments, the demulsifier composition is injected continuously, semi-continuously, or in batch fashion. The injecting is generally accomplished using electric or gas pumps fluidly connected to a source of demulsifier composition. In some embodiments, addition or injection of the demulsifier composition is suitably controlled by one or more digital control mechanisms.

EXPERIMENTAL

Example 1

A 500 mL three necked round-bottom flask was equipped with temperature probe, nitrogen inlet, condenser and magnetic stir bar. Then 190 g 2-ethylhexylglycidyl ether was added to the flask. Then 4-aminophenol was added to flask with good stirring. The mixture was heated to 120° C. under nitrogen blanket and stirred for about 1 hour or until completion of reaction. As reaction proceeded a homogenous dark-amber product was observed to form. The resulting product was characterized by NMR and ESI-MS to have the following structure:

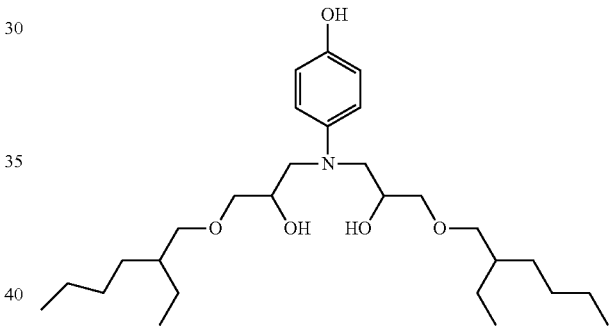

Example 2

The procedure of Example 1 was repeated using butyl glycidyl ether in a 1:1 molar replacement of 2-ethylhexylglycidyl ether. The polymeric product was analyzed by gel permeation chromatography and was found to have a weight average molecular weight of 6996 g/mol and a polydispersity index of 4.9.

Example 3

The procedure of Example 1 was repeated using $C_8$-$C_{10}$ (average carbon chain length) alkyl glycidyl ether in a 1:1 molar replacement of 2-ethylhexylglycidyl ether. The polymeric product was analyzed by gel permeation chromatography and was found to have a weight average molecular weight of 6157 g/mol and a polydispersity index of 3.0.

Example 4

A 1 L four-necked round bottom flask was equipped with an overhead stirrer, $N_2$ purge, temperature probe, and Dean-Stark trap with condenser. Example 1 was repeated, and the entire product obtained was added to the flask, along with 290 g heavy aromatic naphtha (HAN) and 1.5 g of a 50% KOH solution. The overhead stirrer was started along with a very slow nitrogen purge (approximately one bubble per five seconds). The reaction flask was heated to 65° C. Then 20 g of paraformaldehyde was prepared for addition to the flask. Once a consistent temperature of 65° C. was achieved, a first aliquot (about 10 g) of the paraformaldehyde was added to the flask. The temperature was observed to increase 15° C.-20° C. When the exotherm stopped and the reactor returned to 65° C., the remainder of the 20 g of paraformaldehyde was added to the flask. The temperature was observed to increase 1° C.-10° C.

When the exotherm stopped, the set temperature in the flask was changed from 65° C. to 95° C. The flask was then held at 95° C. for 3 hours.

After the 3 hours elapsed, the set temperature of the flask was increased to 180° C. whereupon reflux was observed. Reflux was continued for three hours. At the end of the three-hour reaction period, the heat source was removed and the flask was allowed to cool overnight. The amount of water removed via the Dean-Stark trap was recorded.

The polymeric product was analyzed by gel permeation chromatography and was found to have a weight average molecular weight of 4574 g/mol and a polydispersity index of 2.2.

Example 5

To a 1 L four-necked round bottom flask was added p-N,N-di-[1-(2-ethylhexyloxy)-2-hydroxy-propyl)] aminophenol/formaldehyde resin made by the procedure of Example 1, and potassium hydroxide; the flask was equipped with an overhead stirrer, a nitrogen purge, a Dean-Stark trap with condenser, and a temperature probe. The stirrer was started at moderate speed, as the nitrogen purge was started at a rate of one bubble per second. The water flow was turned on to the condenser and the Dean-Stark trap was filled to the neck with heavy aromatic naphtha. The temperature was set to 150° C. and heating was started. Water was distilled from the base catalyst. A 5 mL sample was collected for Karl-Fischer water analysis. If the sample contained more than 0.1% water, distillation was continued for 30 minutes and analysis was repeated. When the sample contained less than 0.1% water, the flask was cooled to 60° C. Once the reaction mixture reached 60° C., the $N_2$ purge was increased.

Example 6

500 g of the reaction mixture of Example 1, dissolved in HAN and including KOH, was transferred to a 1 L Paar pressure reaction vessel (obtained from the Paar Instrument Company of Moline, IL). The vessel was closed and purged with nitrogen three times, then nitrogen pressure in the flask was set to 5 psi (34 kPa).

The vessel was heated to 150° C. Then ethylene oxide gas was added until the pressure in the vessel was observed to reach 60 psi (414 kPa). The weight of the ethylene oxide added to the reactor was recorded. The pressure was observed to decrease in the vessel over time. When the pressure reached 10 psi (69 kPa), additional ethylene oxide was added until the pressure again reached 60 psi (414 kPa). The pressure was allowed to decrease to 10 psi (69 kPa), followed by addition of ethylene oxide to obtain 60 psi (414 kPa) until the desired amount of ethylene oxide was added and reacted.

Once the desired amount of ethylene oxide was added and reacted, a 50 mL sample was taken under safe conditions. This retrieved aliquot was recorded and the amount of ethylene oxide needed for the next one mole addition of EO was calculated. On the pressure reaching 10 psi, the desired amount of ethylene oxide needed to complete a one-mole addition was added, or until the pressure reached 60 psi. The pressure was allowed to decrease, and the process was continued until the desired amount of ethylene oxide was added and consumed by the reaction. After each pressurization, an aliquot of polymer was removed from the reactor.

Example 7

An amount of the resin formed using the procedure of Example 4 and having a weight average molecular weight ($M_w$) of 4574 g/mol and a polydispersity index (PDI) of 2.2 was divided into seven portions. Using the procedure of Example 6, portions of the resin were reacted with between 8 and 20 moles of ethylene oxide per mole of monomer repeat unit, to obtain Samples DM-1 to DM-7 as shown in Table 1.

TABLE 1

Reaction ratios of the resin of Example 7 with ethylene oxide to form demulsifiers DM-1 to DM-7.

| Demulsifier | Description of reaction |
|---|---|
| DM-1 | 8 moles of ethylene oxide per mole of monomer repeat unit |
| DM-2 | 10 moles of ethylene oxide per mole of monomer repeat unit |
| DM-3 | 12 moles of ethylene oxide per mole of monomer repeat unit |
| DM-4 | 14 moles of ethylene oxide per mole of monomer repeat unit |
| DM-5 | 16 moles of ethylene oxide per mole of monomer repeat unit |
| DM-6 | 18 moles of ethylene oxide per mole of monomer repeat unit |
| DM-7 | 20 moles of ethylene oxide per mole of monomer repeat unit |

Polyethoxylated HCAP resins DM-1 to DM-7 were tested for effectiveness in demulsifying oil-in-water emulsions using the Emulsion Resolution Test outlined below.

Emulsion Resolution Test. A water-in-oil emulsion is prepared by blending 5 mL tap water and 45 mL crude oil, along with 10 ppm by weight (actives) of a selected demulsifier. The mixture is blended in a Waring blender for 30 s at 100% power to form an emulsion. The emulsion is added to a glass tube and capped with a cap having an electrode assembly affixed thereon. The capped tube is placed into a portable electric desalter (PED), which employs constant heating via a heating block designed and adapted to fit closely to the glass tube, and is further adapted to apply a voltage to the contents of the tube via the electrode assembly. The PED heating block is preheated to 120° C. before inserting the tube into the PED. An electric field of 2000 volts is applied to the tube continuously for two minutes, a total of six times during the test, with the voltage applied for two minutes starting at 12, 22, 27, 32, 37, and 42 minutes after insertion of the tube into the PED. The tube is observed at fixed intervals during the testing, and percent water coalescence was monitored over time, wherein percent water coalescence means the volume of the water layer visually separated from the remaining contents of the tube ("resolved" water), as a percent of total volume of the contents of the tube. The total volume of resolved water and the rate of water layer development were used to compare the performance of the demulsifiers in promoting water coalescence.

Using the Emulsion Resolution Test outlined above, demulsifiers DM-2 to DM-7 were tested using a first crude oil having a Crude Oil API of 20.27°. A blank emulsion formed from the crude oil and including no demulsifier was also tested. The results are shown in Table 2.

TABLE 2

Percent water coalescence versus time in minutes for demulsifiers DM-2 to DM-7 as tested in Example 7.

| Demulsifier | Time (minutes) | | | | | | | |
|---|---|---|---|---|---|---|---|---|
| | 5 | 10 | 15 | 20 | 25 | 30 | 35 | 40 |
| None | 0 | 0 | 0 | 1 | 10 | 13 | 56 | 63 |
| DM-2 | 0 | 0 | 3 | 10 | 38 | 44 | 75 | 88 |
| DM-3 | 0 | 0 | 9 | 25 | 50 | 50 | 63 | 63 |
| DM-4 | 0 | 0 | 6 | 13 | 25 | 63 | 63 | 75 |
| DM-5 | 0 | 0 | 13 | 18 | 35 | 63 | 63 | 75 |
| DM-6 | 0 | 0 | 13 | 20 | 50 | 63 | 75 | 75 |
| DM-7 | 0 | 0 | 9 | 13 | 44 | 56 | 63 | 75 |

As shown in Table 2, after 40 minutes of standing, and in some cases after only 15 minutes of standing, the polyalkoxylated HCAP resins all performed to accelerate resolution (coalescence) of the emulsion, or resulted in a greater degree of coalescence than the emulsion alone. After 40 minutes, DM-2 appeared to have optimal properties for resolution of the first crude oil emulsion.

Example 8

Using the Emulsion Resolution Test of Example 7, demulsifiers DM-1 to DM-6 were tested using a second crude oil having a Crude Oil API of 36.1°. The results are shown in Table 3.

TABLE 3

Percent water coalescence versus time in minutes for demulsifiers DM-1 to DM-6 as tested in Example 8.

| Demulsifier | Time (minutes) | | | | | |
|---|---|---|---|---|---|---|
| | 5 | 10 | 15 | 20 | 25 | 30 |
| None | 0 | 0 | 6 | 13 | 25 | 38 |
| DM-1 | 0 | 4 | 10 | 35 | 50 | 63 |
| DM-2 | 0 | 6 | 23 | 38 | 50 | 56 |
| DM-3 | 0 | 3 | 13 | 25 | 38 | 56 |
| DM-4 | 0 | 6 | 23 | 38 | 50 | 56 |
| DM-5 | 0 | 0 | 6 | 13 | 25 | 38 |
| DM-6 | 0 | 10 | 18 | 19 | 25 | 38 |

As shown in Table 3, after 30 minutes of standing, and in some cases after only 10 minutes of standing, the polyalkoxylated HCAP resins all performed to accelerate resolution (coalescence) of the emulsion, or resulted in a greater degree of coalescence than the emulsion alone. After 30 minutes, DM-2 appeared to have optimal properties for resolution of the second crude oil emulsion.

What is claimed is:

1. A polymer comprising a repeat unit having the structure of Formula I, Formula II, or a combination thereof,

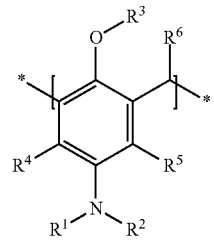

I

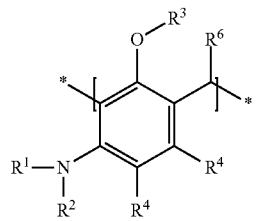

II wherein
$R^1$ and $R^2$ are —$(CR^7R^8)_n(CHOR^9)(CH_2)_p(O)_qR^{10}$;
$R^3$ is $[R^{11}O]_xH$;
$R^4$ and $R^5$ are independently H, $C_1$-$C_{22}$ alkyl, or —$[R^{11}O]_xH$;
$R^6$ is H, alkyl, aryl, benzyl, or aralkyl, optionally substituted with an alkyl group, alkoxy group, or hydroxyl group;
$R^7$ and $R^8$ are independently H or alkyl;
$R^9$ is H or —$[R^{11}O]_xH$;
$R^{10}$ is $C_1$-$C_{24}$ linear, branched, or cyclic alkyl, aryl, or aralkyl;
each $R^{11}$ is independently —$CH_2$—$CH_2$—, —$CH(CH_3)$—$CH_2$—, —$CH_2$—$CH_2$—$CH_2$—, $CH_2$—$CH_2$—$CH_2$—$CH_2$—, or —$CH(C_6H_6)$—$CH_2$—;
n is an integer between 1 and 12;
p is 0 or an integer between 1 and 12;
q is 0 or 1; and
each x is independently an integer between 2 and 1000.

2. The polymer of claim 1 wherein $R^4$ and $R^5$ are H.

3. The polymer of claim 1 wherein $R^7$ and $R^8$ are H.

4. The polymer of claim 1 wherein $R^{10}$ is selected from n-octyl, isooctyl, n-decyl, isodecyl, n-dodecyl, n-tetradecyl, n-hexadecyl, n-hexyl, n-butyl, isobutyl, t-butyl, n-pentyl, isopentyl, or 2-ethylhexyl.

5. The polymer of claim 1 wherein $R^6$ is H, 1.

6. The polymer of claim 1 wherein n, p, and q are 1.

7. The polymer of claim 1 comprising 1-100 of the repeat units.

8. The polymer of claim 1 wherein $R^4$, $R^5$, and $R^9$ are H, and x is an integer between 2 and 20.

9. The polymer of claim 1 further comprising a repeat unit comprising the condensation product of a phenolic compound and an aldehyde.

10. The polymer of claim 9 wherein the phenolic compound is phenol, resorcinol, pyrocatechol, hydroquinone, phloroglucinol, hydroxyhydroquinone, or a combination of two or more thereof.

11. The polymer of claim 9 wherein the aldehyde is formaldehyde, acetaldehyde, benzaldehyde, vanillin, salicylaldehyde, glyoxal, glyoxylic acid, or a combination of two or more thereof.

12. The polymer of claim 1 wherein the polymer excludes repeat units having the structure of Formula II.

13. The polymer of claim 1 wherein each $R^{11}$ is —$CH_2$—$CH_2$—.

14. The polymer of claim 1 wherein each $R^{11}$ is selected from —$CH_2$—$CH_2$— and —$CH(CH_3)$—$CH_2$—.

15. A composition comprising a polymer of claim 1 and a solvent, the composition comprising 1 wt % to 99.9 wt % of the polymer.

16. A composition comprising a crude oil, a wash water, and a polymer of claim 1.

* * * * *